(12) United States Patent
Bradford et al.

(10) Patent No.: US 11,266,548 B2
(45) Date of Patent: Mar. 8, 2022

(54) WOUND DRESSING

(71) Applicant: ADVANCED MEDICAL SOLUTIONS LIMITED, Winsford (GB)

(72) Inventors: Colin Bradford, Keighley (GB); Brian John Hamerslagh, Higher Runcorn (GB)

(73) Assignee: ADVANCED MEDICAL SOLUTIONS LIMITED, Winsford (GB)

( * ) Notice: Subject to any disclaimer, the term of this patent is extended or adjusted under 35 U.S.C. 154(b) by 601 days.

(21) Appl. No.: 15/672,571

(22) Filed: Aug. 9, 2017

(65) Prior Publication Data

US 2018/0042789 A1 Feb. 15, 2018

(30) Foreign Application Priority Data

Aug. 10, 2016 (GB) ...................... 1613744

(51) Int. Cl.
*A61F 13/02* (2006.01)
*A61F 13/537* (2006.01)
(Continued)

(52) U.S. Cl.
CPC .... *A61F 13/53756* (2013.01); *A61F 13/0203* (2013.01); *A61F 13/023* (2013.01);
(Continued)

(58) Field of Classification Search
CPC ................ A61F 13/025; A61F 13/0253; A61F 13/0259; A61F 13/53756; A61F 13/0203;
(Continued)

(56) References Cited

U.S. PATENT DOCUMENTS 4,773,408 A * 9/1988 Cilento ................... A61L 15/26
428/314.4
9,452,088 B2 * 9/2016 Shulman ................. A61F 17/00
(Continued)

FOREIGN PATENT DOCUMENTS

WO WO 01/68021 A1 9/2001
WO 2006/081403 A1 8/2006
(Continued)

OTHER PUBLICATIONS

European Search Report dated Nov. 23, 2017, issued in connection with European Patent Application No. 17185441.7.
(Continued)

*Primary Examiner* — Camtu T Nguyen
(74) *Attorney, Agent, or Firm* — Nixon & Vanderhye P.C.

(57) ABSTRACT

The present invention relates to wound dressings which are particularly useful (but not necessarily exclusively) on moderate to heavily exuding wounds comprising:
an absorbent pad having a first major face comprised of absorbent material and configured for wound contact, and a second major face opposed to the first major face; and
a backing layer bonded to the second major face of the pad;
wherein the pad and the backing layer are sized such that the backing layer extends beyond the periphery of the pad, thereby defining a margin;
wherein the margin of the backing layer is provided with a first adhesive for adhering the backing layer to skin; and
wherein a layer of second, low trauma adhesive is provided on, and in direct contact with, the first major face of the pad for adhering the pad to a wound, said layer
(Continued)

Figure 1:
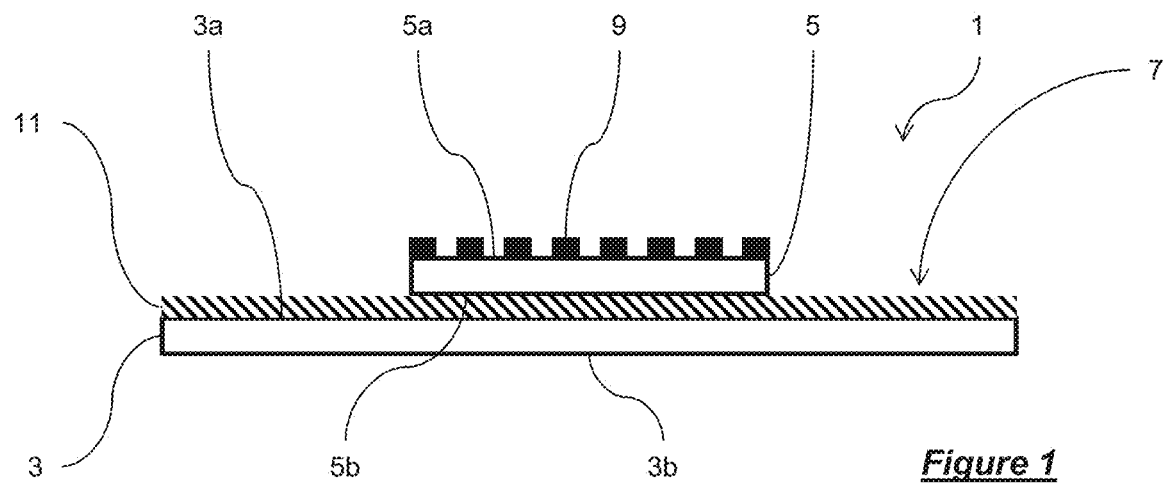

of second, low trauma adhesive being configured to allow passage of exudate from the wound to the absorbent pad.

8 Claims, 1 Drawing Sheet

(51) Int. Cl.
*A61L 15/58* (2006.01)
*A61L 15/60* (2006.01)

(52) U.S. Cl.
CPC ...... *A61F 13/0253* (2013.01); *A61F 13/0259* (2013.01); *A61L 15/58* (2013.01); *A61L 15/60* (2013.01); *A61L 2300/206* (2013.01); *A61L 2300/404* (2013.01)

(58) Field of Classification Search
CPC .... A61L 15/58; A61L 15/60; A61L 2300/206; A61L 2300/404; A61L 15/62; A61L 24/00
See application file for complete search history.

(56) References Cited

U.S. PATENT DOCUMENTS

| | | |
|---|---|---|
| 2001/0051178 A1 | 12/2001 | Blatchford et al. |
| 2003/0007999 A1 | 1/2003 | Blatchford et al. |
| 2004/0089304 A1* | 5/2004 | Barakat ............. A41D 13/1115 128/206.12 |
| 2004/0133143 A1 | 7/2004 | Burton et al. |
| 2006/0057369 A1 | 3/2006 | Hilfenhaus et al. |
| 2010/0030179 A1 | 2/2010 | Burton et al. |
| 2010/0098942 A1* | 4/2010 | Stachnik ................. B60J 11/00 428/351 |
| 2013/0116645 A1* | 5/2013 | Corley .............. A61F 13/00029 604/369 |
| 2013/0123678 A1 | 5/2013 | Carty et al. |
| 2014/0309574 A1* | 10/2014 | Cotton .............. A61F 13/00012 602/44 |
| 2014/0378923 A1* | 12/2014 | Holm ...................... A61L 15/24 604/365 |
| 2015/0133844 A1* | 5/2015 | Montulet ............ A61F 13/0259 602/44 |
| 2015/0203618 A1* | 7/2015 | Allen .................... C08F 220/18 428/354 |

FOREIGN PATENT DOCUMENTS

| | | |
|---|---|---|
| WO | 2006/127292 A1 | 11/2006 |
| WO | 2010/000451 A1 | 1/2010 |
| WO | 2011/095194 A1 | 8/2011 |
| WO | WO 2015/151613 * | 10/2015 |
| WO | 2016/055075 A1 | 4/2016 |
| WO | WO 2016/108041 * | 7/2016 |
| WO | WO 2016/108041 A1 * | 7/2016 |
| WO | WO 2016/108041 A1 * | 7/2016 |
| WO | WO 2016/109418 A1 | 7/2016 |

OTHER PUBLICATIONS

Notice of Opposition dated Jun. 28, 2021 issued in European Application No. 17185441.7 with English translation (76 pages).
Markowska, Katarzyna, et al., "Silver nanoparticles as an alternative strategy against bacterial biofilms", Department of Bacterial Genertics, Institute of Microbiology, Faculty of Biology, University of Warsaw, Warsaw, Poland, ACTA ABP Biochimica Polonica, vol. 60, No. 4/2013, pp. 523-530 (8 pages).
"Das Therapiekonzept für die Wundbehandlung in der Arztpraxis", Das östereochische Gesundheitswesen—ÖKZ , 56, JP [2015], 10, www.schaffler-verlag.com, with English translation thereof (4 pages).
Nachweis einer Waybackmaschine, www.schaffler-verlag.com, 56, JP [2015], 10 (1 page).
HARTMANN WundForum, 2015, with English translation thereof (3 pages).
Datum WundForum, Das HARTMANN-Magazin fr Wundheilung und Wundbehandlung, Edition 1, 2015—$22^{nd}$ year with English translation (60 pages).
Hydroaktive Wundauflagen HydroTac®, Gebrauchsinformation, Hydroaktive Wundauflagen, Last updated: Gebrauchs.info Mar. 2014 with English translation thereof (3 pages).
Ausdruck einer Amazon-Webseite—Amazon website HydroTac comfort, ©1998-2021, Amazon.com, Inc. with English translation thereof (13 pages).
Anlagenkonvolut, Paul Hartmann AG, Postfach 14 20 89504 Heidenheim, HARTMANN Duetschland, Rechung und Auftragsbestätigung, signature block dated Jun. 22, 2021 with English translation thereof (19 pages).

* cited by examiner

WOUND DRESSING

This application claims priority to GB Patent Application No. 1613744.0 filed 10 Aug. 2016, the entire contents of which is hereby incorporated by reference.

The present invention relates to wound dressings for use particularly (but not necessarily exclusively) on moderate to heavily exuding wounds. The wound dressings of the present application have particular (but again not necessarily exclusive) application to wounds on moving body parts (such as the knee, elbow etc.).

Absorbent wound dressings for moderate to heavily exuding wounds typically take the form of so-called "island dressings" comprising an absorbent pad configured for direct wound contact, and an adhesive backing layer extending beyond the periphery of the pad and thereby defining an adhesive border, said border being configured to adhere the dressing to the skin surrounding a wound and to provide a protective barrier to the wound.

Some island dressings can, however, have poor adherence properties, since adhesive material may only be provided around the adhesive border region, rather than on the entire body-contacting portion of the dressing. As a result, a significant proportion of the dressing is not adhesive.

In order to ameliorate this issue, in addition to the border region of the backing layer being provided with an adhesive, the pad of an island dressing may be provided with wound contacting adhesive in order to adhere the pad itself to a wound. Conventional practice in the construction of such dressings is for the pad to be part of a laminate construction comprising, in addition to the pad itself, a film layer which is adhesively bonded (e.g. by means of an acrylic adhesive) to the face of the pad remote from the backing layer and which carries the layer of wound contacting adhesive. Such dressings are typically manufactured by a process including the following steps:
(i) providing the film, on one face thereof, with a layer of adhesive for bonding the film to the pad and, on the other face thereof, with the layer of the wound contacting adhesive;
(ii) perforating the film and associated adhesive layers;
(iii) bonding the adhesive pad to the backing layer; and
(iv) bonding the film to the adhesive pad.

Adhesives suitable for use as the wound contacting adhesive may be impervious to fluid, and hence perforation step (ii) is used in order to provide passages (i.e. "open areas") for exudate to be transmitted from the wound, through the film layer, and to the absorbent pad.

Such dressings have better adhesive properties than those without a wound contacting adhesive on the pad, but do have a number of disadvantages.

Removal of dressings comprising further adhesive film layers can cause pain and/or wound damage (trauma) on removal, since the adhesive on the wound-contacting pad can pull relatively fragile granulating tissue (i.e. new tissue formed during the wound healing process) away from the wound.

Additionally, such dressings are difficult to manufacture, since perforation of the film layer coated with adhesive on both major surfaces thereof is difficult. Since the adhesive sticks to the perforation tool and as a result either the perforated piece may not be removed properly or the adhesive gradually builds up on the perforation tool and eventually causes jamming.

Additionally, perforation of the film layer has practical limits in terms of the degree of "open areas" achievable, thereby limiting the effectiveness of the wound dressing in wound exudate uptake. Perforated film layers are typically able to attain an open area of at most about 20% with greater open areas the film becomes too flimsy to handle in a manufacturing process.

It is an object of the invention to obviate or mitigate the disadvantages mentioned above.

According to a first aspect of the present invention there is provided a wound dressing comprising:
  an absorbent pad having a first major face comprised of absorbent material and configured for wound contact, and a second major face opposed to the first major face; and
  a backing layer bonded to the second major face of the pad;
  wherein the pad and the backing layer are sized such that the backing layer extends beyond the periphery of the pad, thereby defining a margin;
  wherein the margin of the backing layer is provided with a first adhesive for adhering the backing layer to skin; and
  wherein a layer of second, low trauma adhesive is provided on, and in direct contact with, the first major face of the pad for adhering the pad to a wound, said layer of second, low trauma adhesive being configured to allow passage of exudate from the wound to the absorbent pad.

In the context of the present invention, the term "low trauma" is intended to qualify that the second adhesive has a suitable adhesive strength to adhere the pad directly to a wound, but which does not have an adhesive strength which would cause significant pain and/or wound damage (trauma) upon removal. Suitably, the second adhesive may have a peel strength of 0.1-1.0N/2.5 cm. (Peel strengths for the purposes of the present application are determined by using a strip comprising the adhesively coated substrate, the strip having a width of 25 mm and a length of 120-130 mm. For the purpose of testing, the strip is peeled from a clean stainless steel surface and the peel strength is determined using a Lloyds LRX Tensometer with a 50N load cell).

The wound dressings of the present invention offer advantages over prior art dressings, since adhesive is provided both around the margin of the backing layer and also on the adhesive pad itself (collectively referred to hereinafter as the "body-contacting surface" of the wound dressing). This allows for good adherence of the wound dressing to a patient. Such dressings have particular application to wounds on moving body parts (such as the knee, elbow etc.), where strong adhesion is required to maintain the dressing fixed to the body.

Furthermore, the use of low trauma adhesive on the absorbent pad ensures that pain and/or wound damage (trauma) upon removal is mitigated.

Adhesives suitable for use as the second, low trauma adhesive may be impervious to fluid, thereby restricting flow of wound exudate to the absorbent pad on which the second adhesive is applied. To ameliorate this issue, the layer of second, low trauma adhesive may be a discontinuous (i.e. incomplete) layer. Discontinuous layers thereby facilitate passage of wound exudate therethrough and thereby improve uptake of wound exudate by the pad. Such a discontinuous layer may, for example, take the form of a reticulated (net-like) pattern or could take the form of a series of adhesive dots provided on the surface of the pad. Other arrangements will be readily appreciated by those of skill in the art.

The discontinuous layer of second, low trauma adhesive may have an open area of greater than 30% (e.g. greater than 50%) since difficulties with production of apertured films does not apply when the adhesive is provided directly on the pad. The open area may be greater than 30% and may, for example, be 30-60%. This compares with prior art constructions, such as those involving a perforated film adhesive wound-contacting layer, which typically have an open area of only 20%. It will therefore be appreciated that wound dressings according to the present invention which include a discontinuous layer of second adhesive offer particularly improved wound exudate uptake properties as compared with the prior art.

The layer of second, low trauma adhesive is preferably printed onto the first major face of the pad.

The second adhesive may be selected from silicone-based adhesives, sheet hydrogels, polyurethane-based adhesives and modified polyolefin-based adhesives. Adhesives from this list may be selected to have the required low trauma characteristics suitable for use in adhering absorbent pads directly to wounds, while not causing substantial pain and/or wound damage (trauma) upon removal.

The second adhesive is preferably a silicone-based adhesive, since such adhesives do not lose tack (i.e. adhesive strength) when wet. It will be appreciated that the wound-contacting pad, on which the second adhesive is applied, may encounter significant levels of wound exudate in use. It follows that employing an adhesive which maintains tack in such an environment provides particular advantages in providing adhesive wound dressings for use in such applications.

Particularly preferred wound dressings utilise silicone-based second adhesive layers having an open area of greater than 50% in a reticulated or dotted pattern. Such dressings are particularly advantageous in terms of low-trauma properties, since the relatively large open area equates to reduced adhesive coverage (as compared with wound dressings employing perforated adhesive film layers, which typically have open layers of at most 20%), thereby ameliorating issues with pulling fragile granulating tissue from the wound upon dressing removal.

Suitable medical grade silicone adhesives for use in the present invention are obtainable as two part systems from companies such as Bayer or Wacker. For use in the invention, the two part systems are mixed together, printed or coated onto substrate, and then cured by heat.

In the present invention, the layer of second wound-contacting adhesive is in direct contact with the pad, by which we mean that the whole area of the low trauma adhesive is in contact with the absorbent pad. This means that there is no requirement to use further film or other intermediate layers as a carrier for the wound-contacting adhesive, thereby reducing the number of component parts in the dressing. Direct contact also allows alternative manufacturing options for the wound dressings of the present invention as compared with the prior art, thereby ameliorating the aforementioned difficulties in relation to manufacturing.

According to a second aspect of the present invention there is provided a process for manufacturing a wound dressing, the process comprising the steps of:
(a) providing a backing layer;
(b) providing a pad of absorbent material having a first major face comprised of absorbent material and configured for wound contact, and a second major face opposed to the first major face; and
(c) bonding the second major face of the pad of absorbent material to the backing layer;

wherein the pad is provided with a layer of second, low trauma adhesive on, and in direct contact with, the first major face of the pad.

The first major face of the pad of absorbent material may be provided with the layer of second, low trauma adhesive prior to, or after, bonding the second major face of the pad of absorbent material to the backing layer. Preferably the layer of second, low trauma adhesive is provided on the bad prior to bonding. Such a method is particularly beneficial, since the backing layer and pad may be manufactured separately, and then bonded together in order to complete the dressing.

Provision of both the first and second adhesive may be achieved using methods customary to those in the art, including via use of a rotary screen printer, gravure roller, knife over roller, transfer coating, etc. The layer of second, low trauma adhesive is preferably printed onto the first major face of the pad.

The backing layer of the wound dressings of the present invention may be comprised of any suitable material customary to those of skill in the art. The backing layer may be comprised of a flexible material. Suitable materials for use as the backing layer include semi-permeable polyurethane films, semi-permeable membranes or non-woven fabrics. Typically, the backing layer should be comprised of material suitable for providing a waterproof and/or microbial barrier layer over the absorbent pad.

The margin defined by the relative sizing of the pad and backing layer may completely encircle the pad, thereby defining a border.

As mentioned above, the backing layer is also provided with an adhesive (herein referred to as the "first adhesive"). The first adhesive need not be a "low trauma" adhesive, as with the second adhesive, since it is not intended to contact the fragile tissue of a wound directly, but is instead intended to contact relatively strong, intact skin surrounding the wound. As a result, issues with pain and wound damage (trauma) on removal of the dressing are reduced, thereby enabling use of stronger adhesives. Suitably, the first adhesive may have a peel strength of 3.0-7.0N/2.5 cm. The first adhesive may be selected from acrylic-based adhesives, aqueous-based adhesives, and hydrocolloids. Suitable acrylic adhesives are available under the designations "National Starch 380-2819", "Gelva Adhesive 788" and "Gelva Adhesive 737".

The margin of the backing layer and/or the first major face of the pad may be provided with an antimicrobial and/or anti-biofilm agent. Suitable antimicrobial agents include silver, silver compounds, iodine, iodine compounds, or polyhexamethylene biguanide (PHMB).

When antimicrobial agents are used in conjunction with acrylic- or aqueous-based adhesives on the margin of the backing layer, ionic species having antimicrobial properties are able to elute from the margin thereby giving an antimicrobial effect. Provision of antimicrobial on the border thereby assists in preventing ingress of micro-organisms into a wound.

The absorbent pad may be comprised of absorbent polyurethane foam. Polyurethane foam for use in the invention may be produced by procedures that are entirely conventional in the art.

If the foam is the only absorbent in the dressing, then a suitable thicknesses will be 3-5 mm. If the dressing contains a superabsorbent, the foam can be as thin as 1.5 mm.

Bonding of the components of the dressing (e.g. the backing layer and pad) may be achieved by any suitable means. Thus, for example, an entire surface of the backing layer may be provided with a layer of adhesive which functions to provide the first adhesive on the margin of the backing layer and which also functions to bond the absorbent pad and the backing layer together.

Preferred features described above in relation to the first aspect of the present invention also represent preferred features of the second aspect of the present invention (and vice versa), subject to a technical incompatibility that would prevent such a combination of preferred features. Furthermore, it will be evident to the skilled person that advantages set out above in respect of the first aspect of the present invention are also offered by the second aspect of the present invention.

Figure 2:
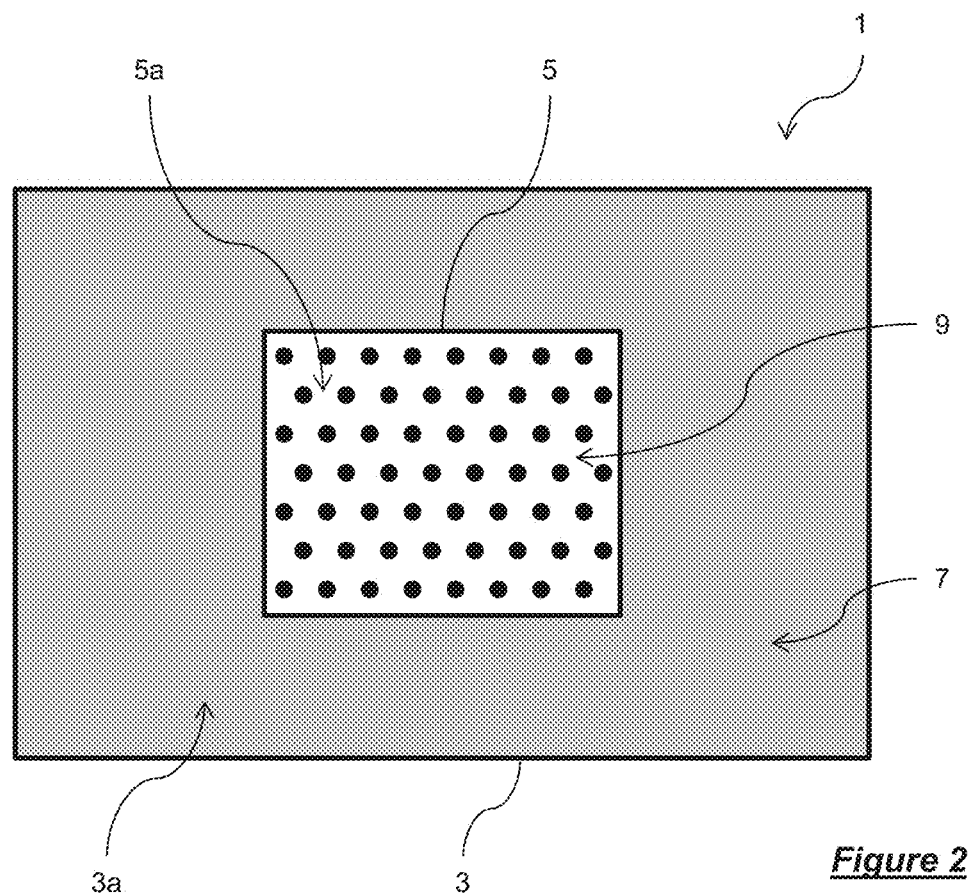

The invention will now be further described, by way of example only, with reference to the accompanying drawings, in which:

FIG. 1 is a schematic sectional view of a wound dressing embodying the first aspect of the present invention, as seen from a side thereof; and FIG. 2 is a schematic top-down view of the wound dressing depicted in FIG. 1.

The figures illustrate a generally rectangular adhesive wound dressing 1 of the "island" type, which has useful application to moderate to heavily exuding wounds, particularly those on moving body parts (such as the knee, elbow etc.).

The wound dressing 1 is a laminate construction comprising a backing layer 3 having an absorbent pad layer 5 disposed centrally thereon and bonded thereto in the manner described below. The backing layer 3 is sized so as to extend beyond the periphery of the pad 5, and thereby defines an exposed border region 3a encircling the pad 5. The exposed border region 7 and the pad 5 are both configured to adhere to the human body in the region of, and surrounding, a wound as explained more fully below.

The absorbent pad 5 is comprised of polyurethane foam. The pad 5 has a first major face 5a configured for wound contact and a second major face 5b opposed thereto.

The wound-contacting face 5a of the absorbent pad 5 is provided with a layer of a silicone-based adhesive 9, for adhering the pad 5 to a wound. Silicone-based adhesives typically have weaker adhesive strength than acrylic-based adhesives, and may be described as "low trauma" adhesives since little (if any) pain and/or wound damage (trauma) is experienced upon dressing removal.

Silicone-based adhesive layers are impervious to liquid, and so in order to facilitate wound exudate uptake by the pad 5, the silicone-based adhesive layer 9 is present on the pad 5 as a discontinuous layer, having so-called "open areas", i.e. openings allowing passage of fluid therethrough.

The backing layer 3 is comprised of polyurethane film. The backing layer 3 has a first major face 3a a second major face 3b opposed thereto, with the entire first major face 3a being coated with an acrylic-based pressure-sensitive adhesive 11 (see FIG. 1). Bonding between the backing layer 3 and pad 5 is achieved by pressing the second major face 5b of the pad 5 into contact with the first major face 3a of the backing layer 3, thereby activating the pressure-sensitive adhesive 11 provided on the backing layer 3.

Since adhesive 11 is applied across the entire surface of the backing layer 3, the adhesive 11 on the exposed border region 7 remains exposed after bonding the relatively smaller absorbent pad 5 to the backing layer 3. This exposed adhesive 11 on the border region 7 is therefore available to adhere the wound dressing to skin when pressed into contact therewith.

In use, the wound dressing 1 may be placed against a wound, with the pad 5 in direct contact with the fragile, granulating wound tissue and the adhesive border 7 of the backing layer 3 being in direct contact with intact skin encircling the wound. The adhesive 11 on the border 7 of the backing layer 3 and the adhesive 9 on the pad 5 cooperate to adhere the dressing 1 to the body. The relatively strong acrylic-based adhesive 11 adheres the border region 7 of the backing layer to the intact skin encircling the wound, while the silicone-based adhesive 9 of the pad 5 bonds to the fragile granulating tissue of the wound.

The illustrated wound dressing is produced by a manufacturing process involving the following steps:

(i) providing a backing layer comprising an acrylic-based adhesive on an entire major face thereof;

(ii) providing a pad of absorbent material having a first major face comprised of absorbent material and printed with silicone-based adhesive, and a second major face opposed to the first major face; and (iii) pressing the second major face of the pad of absorbent material against the major face of the backing layer which is provided with adhesive to effect bonding therebetween.

The following numbered embodiments are also provided:

1. A wound dressing comprising:

an absorbent pad having a first major face comprised of absorbent material and configured for wound contact, and a second major face opposed to the first major face; and a backing layer bonded to the second major face of the pad;

wherein the pad and the backing layer are sized such that the backing layer extends beyond the periphery of the pad, thereby defining a margin;

wherein the margin of the backing layer is provided with a first adhesive for adhering the backing layer to skin; and wherein a layer of second, low trauma adhesive is provided on, and in direct contact with, the first major face of the pad for adhering the pad to a wound, said layer of second, low trauma adhesive being configured to allow passage of exudate from the wound to the absorbent pad.

2. The wound dressing according to embodiment 1, wherein the second adhesive is selected from silicone-based adhesives, sheet hydrogels, polyurethane-based adhesives and modified polyolefin-based adhesives.

3. The wound dressing according to embodiment 1 or 2, wherein the second adhesive is a silicone-based adhesive.

4. The wound dressing according to any preceding embodiment, wherein the layer of second, low trauma adhesive is a discontinuous layer.

5. The wound dressing according to embodiment 4, wherein the discontinuous layer of second, low trauma adhesive has an open area of greater than 50%.

6. The wound dressing according to any preceding embodiment, wherein the layer of second, low trauma adhesive is printed onto the first major face of the pad.

7. The wound dressing according to any preceding embodiment, wherein the second adhesive has a peel strength of 0.1 to 1.0N/2.5 cm.

8. The wound dressing according to any preceding embodiment, wherein the first adhesive has a peel strength of 3.0 to 7.0N/2.5 cm.

9. The wound dressing according to any preceding embodiment, wherein the first adhesive is selected from acrylic-based adhesives, aqueous-based adhesives, and hydrocolloids.

10. The wound dressing according to any preceding embodiment, wherein the margin of the backing layer and/or the first major face of the pad is provided with an antimicrobial agent.

11. The wound dressing according to embodiment 10, wherein the antimicrobial agent is selected from silver, silver compounds, iodine, iodine compounds, or polyhexamethylene biguanide (PHMB).

12. The wound dressing according to any preceding embodiment, wherein the margin of the backing layer and/or the first major face of the pad is provided with an anti-biofilm agent.

13. A wound dressing substantially as hereinbefore described with reference to the figures.

14. A process for manufacturing a wound dressing, the process comprising the steps of:
  (a) providing a backing layer;
  (b) providing a pad of absorbent material having a first major face comprised of absorbent material and configured for wound contact, and a second major face opposed to the first major face; and
  (c) bonding the second major face of the pad of absorbent material to the backing layer;
  wherein the pad is provided with a layer of second, low trauma adhesive on, and in direct contact with, the first major face of the pad.

15. The process for manufacturing a wound dressing according to embodiment 14, wherein the first major face of the pad of absorbent material is provided with the layer of second, low trauma adhesive prior to bonding the second major face of the pad of absorbent material to the backing layer.

The invention claimed is:

1. A wound dressing comprising:
  an absorbent pad having a first major face comprised of absorbent material and configured for wound contact, and a second major face opposed to the first major face; and
  a backing layer bonded to the second major face of the absorbent pad,
  wherein the absorbent pad and the backing layer are sized such that the backing layer extends beyond the periphery of the absorbent pad, thereby defining a margin,
  wherein the margin of the backing layer is provided with a first adhesive for adhering the backing layer to skin and the first adhesive has a peel strength of 3.0N/2.5 cm to 7.0N/2.5 cm,
  wherein a layer of a second adhesive is provided on, and in direct contact with, the first major face of the absorbent pad for adhering the absorbent pad to a wound, and
  wherein the second adhesive is a silicone-based adhesive and has a peel strength of 0.1N/2.5 cm to 1.0N/2.5 cm said layer of the second adhesive being configured to allow passage of exudate from the wound to the absorbent pad and being a discontinuous layer with an open area of greater than 50%.

2. The wound dressing according to claim 1, wherein the layer of the second adhesive is printed onto the first major face of the absorbent pad.

3. The wound dressing according to claim 1, wherein the first adhesive is selected from acrylic-based adhesives, aqueous-based adhesives, and hydrocolloids.

4. The wound dressing according to claim 1, wherein the margin of the backing layer and/or the first major face of the absorbent pad is provided with an antimicrobial agent.

5. The wound dressing according to claim 4, wherein the antimicrobial agent is selected from silver, silver compounds, iodine, iodine compounds, or polyhexamethylene biguanide (PHMB).

6. The wound dressing according to claim 1, wherein the margin of the backing layer and/or the first major face of the absorbent pad is provided with an anti-biofilm agent.

7. A process for manufacturing the wound dressing according to claim 1, the process comprising the steps of:
  (a) providing the backing layer;
  (b) providing the absorbent pad having the first major face comprised of absorbent material and configured for wound contact, and the second major face comprised of absorbent material; and
  (c) bonding the second major face of the absorbent pad of absorbent material to the backing layer,
  wherein the absorbent pad is provided with a layer of a second adhesive on, and in direct contact with, the first major face of the absorbent pad,
  wherein the second adhesive is a silicone-based adhesive and has a peel strength of 0.1N/2.5 cm to 1.0N/2.5 cm,
  wherein the layer of the second adhesive is a discontinuous layer with an open area of greater than 50%,
  wherein the absorbent pad and the backing layer are sized such that the backing layer extends beyond the periphery of the absorbent pad, thereby defining the margin, and
  wherein the margin of the backing layer is provided with the first adhesive for adhering the backing layer to skin and the first adhesive has a peel strength of 3.0N/2.5 cm to 7.0N/2.5 cm.

8. The process for manufacturing a wound dressing according to claim 7, wherein the first major face of the absorbent pad is provided with the layer of the second adhesive prior to bonding the second major face of the absorbent pad of absorbent material to the backing layer.

* * * * *